United States Patent [19]

MacDonald

[11] 4,358,445

[45] Nov. 9, 1982

[54] 6α-FLUORO-PREDNISDONE 17,21 DIESTERS

[76] Inventor: Peter MacDonald, 21/35 Sempione St., Arese (Milano), Italy

[21] Appl. No.: 207,809

[22] Filed: Nov. 17, 1980

[30] Foreign Application Priority Data

Nov. 16, 1979 [IT]  Italy ................................ 27353 A/79
Oct. 9, 1980 [IT]  Italy ................................ 49853 A/80

[51] Int. Cl.$^3$ ............................................ A61K 31/56
[52] U.S. Cl. ................................ 424/243; 260/397.45
[58] Field of Search .................... 260/397.45; 424/243

[56] References Cited

U.S. PATENT DOCUMENTS

| | | | |
|---|---|---|---|
| 3,007,923 | 11/1961 | Muller et al. | 260/239.55 |
| 3,152,154 | 10/1964 | Ercoli et al. | 260/397.45 |
| 3,312,590 | 4/1967 | Elks et al. | 424/243 |
| 3,422,193 | 1/1969 | Shapiro et al. | 260/397.45 |
| 3,463,852 | 8/1969 | Reimann et al. | 424/243 |
| 3,499,016 | 3/1970 | Lincoln et al. | 260/397.45 |
| 3,529,060 | 9/1970 | Ercoli et al. | 424/243 |
| 3,626,063 | 12/1971 | Lincoln et al. | 424/243 |
| 3,691,214 | 9/1972 | Ercoli et al. | 424/243 |
| 3,714,353 | 1/1973 | Lincoln et al. | 424/243 |
| 3,755,302 | 8/1973 | Ercoli et al. | 260/239.55 R |
| 3,780,177 | 12/1973 | Ercoli et al. | 424/243 |
| 3,784,692 | 1/1974 | Ercoli et al. | 424/243 |
| 3,857,941 | 12/1974 | Ercoli et al. | 424/243 |
| 3,980,778 | 9/1976 | Ayer et al. | 260/397.45 |
| 4,024,131 | 5/1977 | Villax | 260/239.55 R |
| 4,036,831 | 7/1977 | Loken et al. | 260/239.55 D |
| 4,255,331 | 3/1981 | MacDonald | 260/397.45 |

FOREIGN PATENT DOCUMENTS

| | | |
|---|---|---|
| 858709 | 3/1978 | Belgium . |
| 25149 A/79 | 8/1979 | Italy . |
| 26227 A/79 | 10/1979 | Italy . |
| 7902333 | 3/1979 | Netherlands . |
| 933859 | 8/1959 | United Kingdom . |
| 1403962 | 8/1975 | United Kingdom . |
| 1520356 | 8/1978 | United Kingdom . |
| 2018258 | 4/1979 | United Kingdom . |

OTHER PUBLICATIONS

Steroids; 16:6, 663 (1970), Gene DiPasquale, Charles L. Rassaert and Edward McDougall, Warner-Lambert Research Institute.
"Anti-Inflammatory Agents," Chemistry and Pharmacology, vol. 1, Robert A. Scherrer (cd.) and Michael W. Whitehouse, (1974), Ch. 9, Anti-Inflammatory Steroids, pp. 245 et seq.
Journal of the Amer. Chem. Soc., 82, 4012 (1960).
Harris, D., "Properties and Therapeutic Uses of Corticosteroids with Enhanced Topical Potency", *J. of Steroid Biochemistry,* 6:711–716 (1975).
Gardi, et al., Journal of Medicinal Chemistry, 15, 556 (1972).

*Primary Examiner*—Elbert L. Roberts
*Attorney, Agent, or Firm*—Woodcock, Washburn, Kurtz, Mackiewicz & Norris

[57] ABSTRACT

The present application relates to novel 6α-fluoro prednisolone 17, 21-diesters, to pharmaceutical compositions comprising such diesters, and to methods of treating inflammatory conditions with such diesters.

4 Claims, No Drawings

6α-FLUORO-PREDNISDONE 17,21 DIESTERS

BACKGROUND OF THE INVENTION AND PRIOR ART

During the 1950's and 1960's many pharmaceutical concerns launched extensive programs to synthesize modified corticosteroids. The objective was to create systemically active compounds having more potent anti-flammatory activity than the naturally occuring corticoids but without correspondingly elevated levels of side effects such as interference with the pituitary-adrenal relationship (leading to adrenal insufficiency) and effects on electrolyte balance and glucose metabolism.

The initial efforts resulted in certain quite potent compounds of the prednisolone series having a 9αfloro constituent in combination with 16-α or β-methyl or 16αhydroxy substitution, such as Betamethasone, dexamethasone, and triamcinolone. Certain compounds having 16-αmethyl substitution along with a 6αfloro substituent (paramethasone) or with combined 6α, 9αfloro substitution (flumethasone) also proved interesting. Prednisolone derivitives having a 6αfloro substituent and 16β-methyl substitution were apparently not explored and these are the subjects of this invention. In the above noted prior art compounds, the problem of electrolyte imbalance (primarily sodium retention with potassium depletion) was substantially reduced. Various theories were advanced for this with one or more groups being said to enhance potency ($\Delta'$ and 9αF) either with (9αF) or without ($\Delta'$) some degree of potentiation of mineralcorticoid activity and with other substituents (16-OH,αCH$_3$ or βCH$_3$) being said to attenuate somewhat the mineralcorticoid effect. In any event, when the lower doses made possible by enhanced potency were used, observed electrolyte activity was reduced and it is generally accepted today that at therapeutic doses the compounds which are $\Delta'^4$ dienes with 6α and/or 9αhalogen substitution combined with 16-methyl or 16αhydroxy substitution do not cause an unacceptable degree of electrolyte imbalance.

Despite these early successes, significant separation of other side effects, such as glycogen diposition, from therapeutic activity proved difficult. It was later noted that in some cases the 16αmethyl substitution could, by itself, be employed to augment anti-inflammatory activity somewhat more than glycogen deposition and that 16βmethyl substitution could be employed to diminish glycogenic properties somewhat without altering the anti-inflammatory activity.

The above noted first prepared modified cortosteroids and their esters and other derivatives are still widely used today in various forms, and betamethasone and its esters still represent today almost one-third of the prescriptions written in the United States for topical steroids. Dexamethasone, fluromethasone and paramethasone are also still used clinically today, although to a much lesser degree.

Despite: (1) the above general and accepted statements about the relationship of structure and biological activity (2) the initial and continued success for almost twenty years of Betamethasone (9αdifloro 16β-methyl prednisolone) and its esters as topical anti-inflammatory agents and (3) the use for over a decade of paramethasone acetate (6αFloro-16αmethyl-prednisolone-21-acetate) as a systemic anti-inflammatory agent, there remarkably appears to have been no discovery of the 6α-floro-16β-methyl-prednisolone or its esters.

In the mid-1960's, attention turned to attempts at development of highly effective topical corticoids with little or no systemic effects. The former objective was pursued through a combination of potentiated anti-inflammatory activity per se and/or improved absorption through the stratum corneum. The latter objective was pursued through reduction of systemic activity per se and/or reduction in the ability to migrate from the epidermis into the dermis after penetration of the stratum corneum.

Two important corticoids developed at that time which are still major factors today are the 16-17 acetonides of Triamcinolone and its 6α, 9αdifloro counterpart, fluocinolone. For some reason, still not fully understood, triamcinolone acetonide is about ten times as active as Triamcinolone topically, but only equiactive systemically. Fluocinolone acetonide is essentially ineffective systemically even though it is perhaps even more active topically than its Triamcinolone counterpart. For topical steroids these compounds plus related Fluandrenalone (6αF, 16αOH, hydrocortisone 17,21 acetonide) today represent more than one half of all prescriptions in the United States. While due to the acetonide formation they differ significantly in structure from the compounds of this invention, they are mentioned here because of their importance in the over-all mileau.

At the end of the 1960's, much attention was given to the esters of the earlier discussed compounds and of other compounds, such as beclomethasone (the resulting dipropionate), which had not found earlier commercial use. In some, but by no means all instances, the esterification at 17 and/or 21 was found to improve the potency of therapeutic effect as evaluated by Vasoconstriction assays. What is most striking from the literature of that time is the unpredictability of the results of esterification when trying to apply knowledge gained with one skeletal series to another skeletal series. Mostly this is due to the subtle alteration of the shapes of molecules caused by even minor structural differences and it is on the basis of shape that hormones are recognized by their receptors.

One of the most completely explored series of esters is those of Betamethasone (9αF, 16β- CH$_3$). When esterified in the 17 position, betamethasone is potentiated from activity of 1% of fluocinalone acetonide to up to 350% of fluocinolone acetonide as the ester chain increases from acetate through butyrate and propionate up to valerate, the latter compound being one of the most widely used topical anti-inflammatory agents today. The 17-benzoate, U.S. Pat. No. 3,529,060, has recently been found to be of equal activity to the valerate. Esterification in the 21-position also causes some potentiation of anti-inflammatory activity, but primarily imparts more long acting effects as was expected, from early findings, mentioned previously, on the 21-acetates of betamethasone. As noted earlier, the esters of Betamethasone today represent almost one-third of prescriptions for topical steroids in the United States.

Another series receiving a lot of attention were the 6,9 difloroprednisolones (16 unsubstituted) through the work of Gardi, et al described for example in the Journal of Medicinal Chemistry, 15, 556 (1972) and 15,783 (1972), in Steroids, 16:6, 663 (1970), and in U.S. Pat. Nos. 3,780,177 (6,9 difloroprednisolone 17-butyrale, 21-acylates), 3,784,692 (the corresponding 17 propionates, 21 acylates), 3,691,214 (17-valerates) and 3,857,941 (17-benzoates). Commercial uses of these compounds has not yet begun in the United States.

Finally, the diacetate of 6,9 difloro-16βmethyl prednisolone was discovered by Upjohn to be a very interesting compound subsequently commercialized in the United States. However, none of the other esters seem to have received attention.

An excellent summary of the history of structural modifications of corticosteroids appears as Chapter 9, Anti-inflammatory Steroids, in Anti-Inflammatory Agents, Scheerer (Ed), Academic Press (1974).

This relative activity is surprising since in the 9α-Floro compounds the 16α-methyl series (Dexamethasone) are known to be more active than the 16βmethyl series (betamethasone).

As noted earlier, I have now discovered the 6αFloro, 16βmethyl prednisolone diesters and have found that these compounds are important anti-inflammatory agents, certain of which are of superior potency to 6αfloro, 16αmethyl counterparts in the cotton pellet granuloma rat assay and quite active in the modified McKensie vasoconstriction assay in man. In addition, unlike paramethasone per se, certain members of the series exhibit only limited effect on the thymus and adrenal glands.

DETAILED DESCRIPTION OF THE INVENTION

The invention relates to novel 6α-fluoro-prednisolone 17,21-diesters having the formula I,

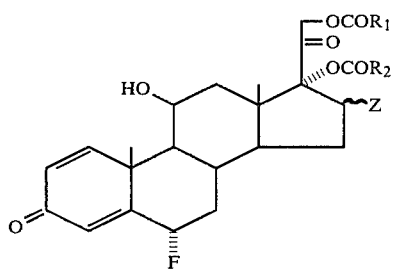

in which $R_1$ and $R_2$ are alkyl groups containing 1-6 carbon atoms or aryl groups, Z is a βmethyl group.

The compounds of formula I are prepared using known methods from the 6α-fluoro-9β,11β-epoxypregna-1,4-dienes having the general formula II.

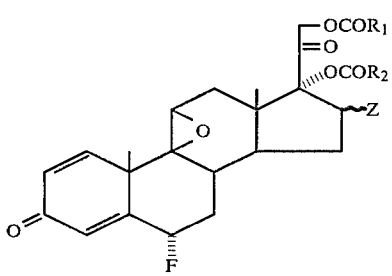

where $R_1$, $R_2$ and Z have the meanings given above,

In our Italian application No. 25149 A/79 there is described a novel and general method for the preparation of the compounds of Formula II, from the corresponding 3-acetoxy-9β,11β-epoxy-pregna-1,3,5-trienes of general formula III

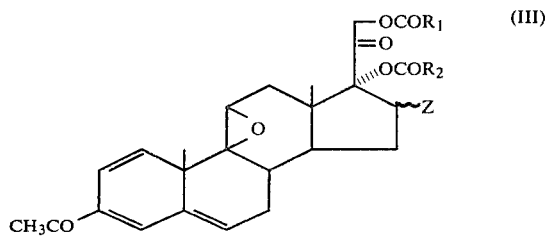

where $R_1$, $R_2$, and Z have the meanings given above. In our Italian application No. 26227 A/79 there is described an alternative method for the preparation of 6α-fluoro-9β,11β-epoxy-pregna-1,4-dienes having the general formula II from the corresponding 1,2-dihydro-compounds having the general formula IV,

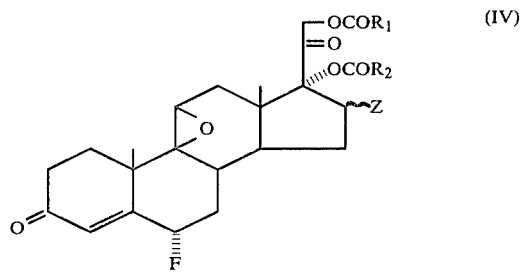

where $R_1$, $R_2$, and Z have the meanings given above. In the above-mentioned applications there is also described the conversion of certain compounds of general formula II, into known corticoids such as diflorasone diacetate and 6α,9α-difluoroprednisolone 17,21-diacetate.

Although the preferred method for preparing the compounds of general formula I is from the corresponding 9β,11β-epoxide of general formula II, in certain cases other methods may be conveniently used. Thus, the novel 6α-fluoro-prednisolone 17,21-diesters of general formula I may be obtained from the corresponding 6α-fluoro-prednisolone by conversion to a 17,21-alkylorthoalkanoate ester by known procedures, followed by cleavage thereof with acid using known techniques to give the corresponding 17-alkanoate ester, followed by acylation in position 21 using standard procedures.

Another method for the preparation of the compounds of general formula I which may occasionally be convenient is by dehydrogenation of the corresponding 1,2-dihydro compounds having the general formula V,

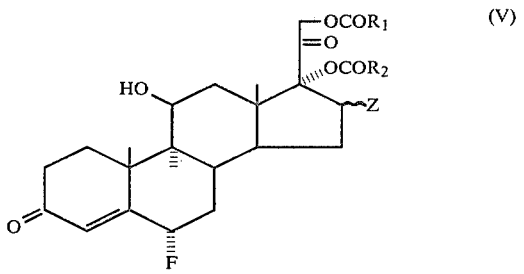

where $R_1$, $R_2$, and Z have the meanings given above, using either chemical or microbiological methods. The preparation of the compounds having the general formula V from the corresponding compounds of general formula IV is described in our Italian appln. 26227 A/79. However it has been found that the dehydrogenation of the compounds of general formula V with dichlorodicyanobenzoquinone (which is the preferred chemical agent for dehydrogenation) shows rather low yields (70–80%); while the same method of dehydrogenation, applied to the compounds of general formula IV, gives 1,4-dienes of formula II in high yields (90–95%). Thus the preferred route from compound IV to compound I is usually via compound II rather than via compound V.

Preferred compounds of formula I include: the 21-acetate, 21-propionate, 21-butyrate, 21-isobutyrate, and the 21-valerate ester derivatives of 6α-fluoro-16β-methyl-prednisolone 17-acetate
6α-fluoro-16β-methyl-prednisolone 17-propionate
6α-fluoro-16β-methyl-prednisolone 17-butyrate
6α-fluoro-16β-methyl-prednisolone 17-valerate
6α-fluoro-16β-methyl-prednisolone 17-benzoate Of the foregoing compounds particularly valuable are the following ones (indicated with a reference number):

(109) 6α-fluoro-16β-methyl-prednisolone 17,21-diacetate (110) 6α-fluoro-16β-methyl-prednisolone 17,21-dipropionate (111) 6α-fluoro-16β-methyl-prednisolone 17-valerate 21-acetate (112) 6α-fluoro-16β-methyl-prednisolone 17-benzoate 21-acetate The present invention includes within its scope the method of treating an inflammatory condition in a warm-blooded animal responsive to treatment with anti-inflammatory agents which comprises administering to said animal a non-toxic, anti-inflammatory effective amount of a 6α-fluoro-prednisolone 17,21-diester of general formula I. The preferred compounds of formula I are valuable anti-inflammatory agents when administered topically, or locally, since they have high anti-inflammatory action as well as low glucocorticoid action on topical administration, and moreover have low glucocorticoid activity when administered systemically. The compounds thus have the desirable high anti-inflammatory action on topical application with little risk of disturbance of the mineral balance or other systemic action should the compound be absorbed.

The 6α-fluoro-prednisolone 17,21-diesters of formula I may be applied topically or locally in any of the conventional pharmaceutical forms, including ointments, lotions, creams, sprays, powders, drops (ear drops or eye drops), suppositories, tablets, pellets, or aerosols.

BIOLOGICAL ACTIVITY

The biological activity of the compounds of the invention was compared to that of beclomethasone dipropionate using the cotton pellet granuloma assay. Female rats (Sprague-Dawley) weighing about 135 g were used and into each animal, under ether anaesthesia, was implanted subcutaneously a cotton pellet weighing 10 mg. The cotton pellets were previously soaked with 25 ml of a solution of the test substance and with 50 ml of a 2% carrageen suspension and left to dry. The cotton pellets contained 0.1, 1, or 10 mcg of the test substance (ten animals were used for each concentration of each substance).

After seven days the animals were sacrificed and the granulomas that had formed around the cotton pellets were removed, dried at 80° and weighed. The adrenal and thymus glands were also removed and weighed.

A similar procedure was carried out using beclomethasone dipropionate, and paramethasone dipropionate, as well as a control.

The results are summarized in Table 1, with the corresponding reference numbers.

It is seen from these results that the compounds cause up to 46.4% inhibition of granuloma formation at dosages of 0.1 mcg/rat whereas beclomethasone dipropionate and paramethasone dipropionate were inactive at this low dosage.

The more active compounds have an activity comparable with almost 100-fold dosages of beclomethasone dipropionate. Notwithstanding this elevated antiinflammatory potency the compounds of the invention usually had minimal effects on the weights of the thymus and adrenal glands even at levels 100 times greater than the effective anti-inflammatory dosages.

The direct applicability of the anti-inflammatory activity to man is tested using the modified McKenzie/Slaughton procedure on thirty human volunteers. Various concentrations of the compounds to be tested are prepared in alcoholic solution and placed under occulusion on intact skin of the forearms of the subjects. After 18 hours the covering is removed and the skin surfaces examined for the intense blanching indications of vasoconstriction. The examination is performed by three independent observers who scored the degree of blanching from zero to three based on blanching within each subject. Thus the maximum score is 90.

To confirm the observations of the cotton pellet granuloma rat assay, one of the compounds of this invention was so tested as were several reference anti-inflammatory compounds in routine clinical use today. The results are shown on Table 1A.

TABLE 1A

| Compound | Concentration gm/ml | Score as % of maximum |
|---|---|---|
| "110" (6αFloro 16βmethyl-17,21 dipropionate) | $10^{-5}$ | 44 |
| | $10^{-6}$ | — |
| | $10^{-7}$ | 12 |
| Diflorasone Diacetate (6,9 difloro- 16βmethyl diacetate) | $10^{-5}$ | — |
| | $10^{-6}$ | — |
| | $10^{-7}$ | 13 |
| Beclomethasone Dipropionate | $10^{-5}$ | — |
| | $10^{-6}$ | — |
| | $10^{-7}$ | 11 |

The results for compound 110 indicate that the compounds of this invention are by any standard potent vasoconstrictors.

TABLE 1

| | | % variation with respect to the controls | | |
|---|---|---|---|---|
| Compound | Dose (mcg/rat) | cotton pellet | adrenal gland | thymus gland |
| paramethasone dipropionate | 0.1 | +0.9 | +0.4 | −2.3 |
| | 1 | −2.2 | −1.6 | −2.6 |
| | 10 | −5.0 | 0 | −3.8 |
| "110" | 0.1 | −46.4 | −2.6 | −4.0 |
| | 1 | −48.8 | −2.2 | −3.1 |
| | 10 | −54.1 | −7.5 | −1.6 |
| BECLOMETA- SONE DI- PROPIONATE | 0.1 | −0.6 | −1.4 | −3.3 |
| | 1 | −12.7 | +0.1 | −0.5 |
| | 10 | −55.0 | −1.7 | −4.7 |

Also within the scope of the invention are pharmaceutical compositions for use in the treatment of inflammatory conditions comprising an effective amount of one or more of the novel compounds of the invention, together with a compatible pharmaceutically-acceptable carrier.

The pharmaceutical dosage forms are prepared according to procedures well known in the art and, where suitable, may contain other active ingredients e.g. antibiotics.

The following, non-limiting, examples illustrate topical formulations prepared in accordance with the invention:

| (a) Inhalation aerosol | |
|---|---|
| 6α-fluoroprednisolone 17,21-diester | 1–10 mg |
| oleic acid | 0.5 mg |
| trichlorofluoromethane | 3000 mg |
| dichlorofluoromethane | 7500 mg |
| (b) Lotion | |
| 6α-fluoroprednisolone 17,21-diester | 0.05–5.0 mg |
| ethyl alcohol | 400 mg |
| polyethylene glycol 400 | 300 mg |
| hydroxypropyl cellulose | 5 mg |
| propylene glycol | 300 mg |
| (c) Glycol ointment | |
| 6α-fluoroprednisolone 17,21-diester | 0.05–5.0 mg |
| hexylene glycol | 100 mg |
| propylene glycol monostearate | 20 mg |
| white wax | 60 mg |
| white petrolatum | 880 mg |

The processes described above are illustrated in the Examples below but should not be construed as limiting the invention, equivalents thereof and products produced thereby which will be obvious to one skilled in the art being considered as part of the invention.

Preparation I

To a suspension of 100 g of 9β,11β-epoxy-16β-methyl-pregna-1,4-diene-17,21-diol-3,20-dione, prepared as described in Journal of the American Chemical Society, 82, 4012 (1960), in 800 ml of dry tetrahydrofuran and 150 ml of triethylorthopropionate at 20° was added 1 g of para-toluenesulphonic acid. After 1 hr the reaction mixture was neutralized with potassium acetate and diluted with water. The precipitate was collected, washed with water, and dried under vacuum to give in quantitative yield 9β,11β-epoxy-16β-methyl-pregna-1,4-diene-17,21-diol-3,20-dione 17,21-ethylorthopropionate. This latter compound was suspended in a mixture of 1 lt of methanol, 0.5 lt water and 5 ml glacial acetic acid and heated under reflux for 4 hr. The reaction mixture was then cooled to 20° and poured slowly into water (6 lt) under strong agitation. The resulting precipitate was collected, washed with water, and dried under vacuum to to give 9β,11β-epoxy-16β-methyl-pregna-1,4-diene-17,21-diol-3,20-dione 17-propionate (113 g), m.p. 150° (d), $[\alpha]_D$ +47.5° (C=1, CHCl$_3$). This compound has not previously been described.

In a similar manner, but instead of triethylorthopropionate using triethylorthoacetate, trimethylorthobutyrate, trimethylothovalerate, or trimethylorthobenzoate, there were obtained the 17-acetate, 17-butyrate, 17-valerate, and 17-benzoate, respectively, of 9β,11β-epoxy-16β-methylpregna-1,4-diene-17,21-diol-3,20-dione.

Preparation 2

To a solution of 113 g of 9β,11β-epoxy-16β-methyl-pregna-1,4-diene-17,21-diol-3,20-dione 17-propionate, prepared as described in Preparation 1, in 500 ml dry pyridine at 0° was added dropwise 75 ml of propionic anhydride and the mixture was allowed to stand at 20°–25° for 3 hr and then poured onto a mixture of ice/water/hydrochloric acid. The precipitate was collected, washed to neutrality with water, and dried under vacuum to give 122 g of 9β,11β-epoxy-16β-methyl-pregna-1,4-diene-17,21-diol-3,20-dione 17,21-dipropionate, m.p. 138°–140° C.

A sample crystallized from ethyl acetate-hexane had m.p. 148° C., $[\alpha]_D$ +40° (C=1, CHCl$_3$).

In a similar manner, but using the appropriate acyl or aroyl chloride or anhydride together with the appropriate 17-ester of 9β,11β-epoxy-16β-methyl-pregna-1,4-diene-17,21-diol-3,20-dione, prepared as described in Preparation 1, there were obtained the 17,21-diacetate, 17-butyrate 21-acetate, 17-valerate 21-acetate, and 17-benzoate 21-acetate of 9β,11β-epoxy-16β-methyl-pregna-1,4-diene-17,21-diol-3,20-dione.

EXAMPLE 1

A mixture of 20 g of 9β,11β-epoxy-16β-methyl-pregna-1,4-diene-17,21-diol-3,20-dione 17,21-dipropionate, prepared as described in Preparation 2, and 2 g of paratoluensulphonic acid in 200 ml of isopropenyl acetate was heated under reflux for 2 hr, neutralized with 20 g of potassium acetate, and evaporated to dryness under reduced pressure. The residue was dissolved in ethanol (200 ml) and treated at 0° for 16 hr with 10 g of perchloryl fluoride. The reaction mixture was then poured into 1 lt of iced water and the resulting precipitate was collected, washed thoroughly with water, and dried under vacuum to constant weight (22 g) to give 6α-fluoro-9β,11β-epoxy-16β-methyl-pregna-1,4-diene-17,21-diol-3,20-dione 17,21-dipropionate. A sample crystallized from methanol had the following characteristics: m.p. 210°.

$[\alpha]_D$ +47.5 (C=1, CHCl$_3$).

$\nu_{max}$ 1765, 1740, 1675, 1640, 1620, 1250-1225 cm$^{-1}$.

$\lambda_{max}$ 245 nm (ε16,500).

In a similar manner, but starting from the 17,21-diacetate 17-propionate 21-acetate, 17-butyrate 21-acetate, 17-valerate 21-acetate, and 17-benzoate 21-acetate diesters of 9β,11β-epoxy-16β-methyl-pregna-1,4-diene-17,21-diol-3,20-dione, prepared as described in Preparation 2, there were obtained the 17,21-diacetate, 17-propionate 21-acetate, 17-butyrate 21-acetate, 17-valerate 21-acetate, and 17-benzoate 21-acetate diesters, respectively, of 6α-fluoro-9β,11β-epoxy-16β-methyl-pregna-1,4-diene-17,21-diol-3,20-dione. (Table 2).

EXAMPLE 2

Following the general procedure of Example 1 and making non-critical variations, but using 9β,11β-epoxy-16α-methyl-pregna-1,4-dione-17,21-diol-3,20-dione 17,21-diacetate, prepared as described in Preparation 2, as the reactant there was obtained 6α-fluoro-9β,11β-epoxy-16α-methyl-pregna-1,4-diene-17,21-diol-3,20-dione 17,21-diacetate in high yield. A sample crystallized from methanol had the following characteristics: m.p. 175°–176°.

$\lambda_{max}$ 244 nm (ε16,800).

$[\alpha]_D$ +5°(C=1, dioxane).

In a similar manner, but starting from the 17,21-dipropionate, prepared as described in Preparation 2, there were obtained the 17,21-dipropionate.

EXAMPLE 3

To a solution of 6α-fluoro-9β,11β-epoxy-16β-methyl-pregna-1,4-diene-17,21-diol-3,20-dione 17,21-diacetate (50 g), prepared as described in Example 1, in 500 ml glacial acetic acid at <5° is added 16.5 ml of a 40% w/v solution of hydrogen bromide in acetic acid. The solution is kept 2 hr at 0°-5° and then poured into water and the precipitate of 6α-fluoro-9α-bromo-16β-methyl-prednisolone 17,21-diacetate is collected, washed with water and dried under vacuum at 30°.

A mixture of the above product (40 g), azobisisobutyronitrile (1 g), and tributyltin hydride (40 ml) in dry tetrahydrofuran (600 ml) was heated under reflux for 4 hr and then evaporated to dryness.

The oily residue crystallized on treatment with heptane (250 ml) and the precipitate was collected, washed thoroughly with heptane, and then dried under vacuum to give 28 g of 6α-fluoro-16β methyl-prednisolone 17,21-diacetate.

In a similar manner, but starting with the 17,21-diacetate, 17,21-dipropionate, 17-butyrate 21-acetate, 17-valerate 21-acetate, and 17-benzoate 21-acetate diesters of 6α-fluoro-9β,11β-epoxy-16β-methyl-pregna-1,4-dione-17,21-diol-3,20-dione, prepared as described in Example 1, there were obtained the corresponding 17,21-diesters of 6α-fluoro-16β-methyl-prednisolone. (Table 3).

TABLE 2

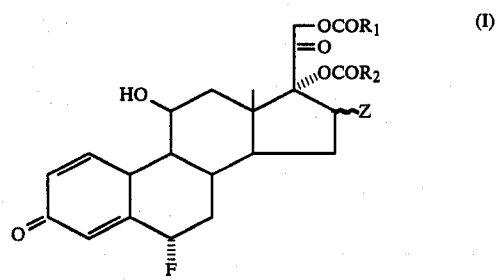

| $R_1$ | $R_2$ | Z | m.p. | $[\alpha]_D$ (solvent) |
|---|---|---|---|---|
| $C_2H_5$ | $C_2H_5$ | β-$CH_3$ | 210° | +47.5° (chloroform) |
| $CH_3$ | $CH_3$ | β-$CH_3$ | 229°(d) | +51° (chloroform) |
| $CH_3$ | $C_2H_5$ | β-$CH_3$ | 150° | +43° (chloroform) |
| $CH_3$ | $C_4H_9$ | β-$CH_3$ | 171° | +40° (chloroform) |
| $CH_3$ | $C_6H_5$ | β-$CH_3$ | 239-240° | +33° (chloroform) |

TABLE 3

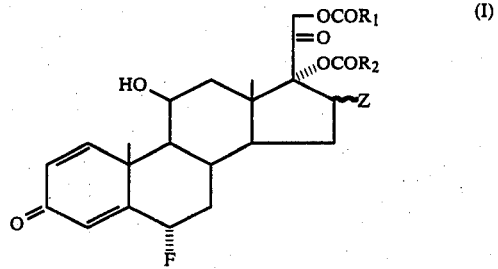

| $R_1$ | $R_2$ | Z | m.p. | $[\alpha]_D$ |
|---|---|---|---|---|
| $C_2H_5$ | $C_2H_5$ | β-$CH_3$ | 245-246° | +67.5° |
| $C_2H_5$ | $C_2H_5$ | α-$CH_3$ | 155-157° | +51° |

Rotations measured in dioxan
Melting points measured in open capillaries.

I claim:

1. A novel 6α-fluoro-prednisolone 17,21-diester of the formula I (I)

in which the $R_1$ group contains 1 carbon atom and the $R_2$ group contains 4 carbon atoms, and wherein Z is a 16β methyl group, whereby said diester is a 6α-fluoro-16β-methyl-prednisolone 17-valerate 21-acetate.

2. A novel 6-α-fluoro-prednisolone 17,21-diester of the formula I (I)

in which the $R_1$ group contains one carbon atom and $R_2$ is a phenyl group, and wherein Z is a 16β methyl group, whereby said diester is a 6-α-fluoro-16-β-methyl-prednisolone 17-benozate 21-acetate.

3. Pharmaceutical compositions for use in the treatment of inflammatory conditions, comprising an effective amount of a compound as claimed in claims 1 or 2, together with a compatible, pharmaceutically acceptable carrier or coating.

4. Method of treating an inflammatory condition in a warm-blooded animal responsive to treatment with anti-inflammatory agents, which comprises administering to said animal a non-toxic, anti-inflammatory effective amount of a compound as claimed in claims 1 or 2.

* * * * *